United States Patent [19]

Gutierrez

[11] 4,389,900
[45] Jun. 28, 1983

[54] CAPACITANCE PROBE SENSOR DEVICE

[75] Inventor: Manuel Gutierrez, Golden, Colo.

[73] Assignee: The United States of America as represented by the Secretary of the Interior, Washington, D.C.

[21] Appl. No.: 219,705

[22] Filed: Dec. 24, 1980

Related U.S. Application Data

[63] Continuation-in-part of Ser. No. 481,408, Jun. 14, 1979, abandoned.

[51] Int. Cl.³ .................... G01F 1/34; G01F 1/00
[52] U.S. Cl. .................... 73/861.42; 73/304 C; 324/61 P; 361/285
[58] Field of Search ............ 73/304 C, 861.65, 861.42, 73/227, 215; 324/61 P; 361/284

[56] References Cited

U.S. PATENT DOCUMENTS

| | | | |
|---|---|---|---|
| 1,571,293 | 2/1926 | Moss | 73/227 |
| 2,720,624 | 10/1955 | Gunst et al. | 324/61 R |
| 2,768,368 | 10/1958 | Crane, Jr. et al. | 73/304 C X |
| 2,774,959 | 12/1956 | Edelman et al. | 324/61 Q S |
| 2,817,234 | 12/1957 | Campbell | 361/284 X |
| 2,910,940 | 11/1959 | Colman et al. | 73/304 C X |
| 2,950,601 | 8/1960 | Wightman | 324/61 R X |
| 3,189,802 | 6/1965 | Zisman | 324/61 R X |
| 3,475,960 | 11/1969 | Miller | 73/301 |
| 3,681,988 | 8/1972 | McNulty | 73/861 |
| 3,863,147 | 1/1975 | Erath | 324/61 R X |
| 3,864,974 | 2/1975 | Ranchwerger | 73/304 C |
| 3,878,719 | 4/1975 | Luttmann et al. | 73/304 C |
| 3,918,306 | 11/1975 | Maltby | 73/304 C |
| 3,958,159 | 5/1970 | Rauchwerger | 361/284 |
| 4,010,650 | 3/1977 | Piatkowski, Jr. | 73/304 C |
| 4,025,846 | 5/1977 | Franz et al. | 324/61 P |
| 4,086,528 | 4/1978 | Walton | 73/304 C X |
| 4,122,718 | 10/1978 | Gustafson | 73/304 C |

FOREIGN PATENT DOCUMENTS 925656  5/1963  United Kingdom ............. 324/61 R Primary Examiner—Daniel M. Yasich
Attorney, Agent, or Firm—Thomas Zack; Donald A. Gardiner

[57] ABSTRACT

A capacitance probe sensor device is disclosed which has a probe formed of KYNAR insulated wire spaced from an uninsulated metallic ground electrode. An oscillator and associated capacitance-resistance network connected to the probe serve to provide a linear output voltage proportional to the change of capacitance between the insulated wire and the ground electrode. The capacitance probe sensor device can be used in a number of applications. They include the measurement of water level, the determination of a liquid's flow rate, and the moisture content of soil.

3 Claims, 7 Drawing Figures

CAPACITANCE PROBE SENSOR DEVICE

This application is a continuation-in-part of U.S. patent application Ser. No. 48,408, filed June 14, 1979, now abandoned.

FIELD OF THE INVENTION

This invention relates generally to apparatus for measuring the change of capacitance between two bodies, and more particularly, to the measurement of the change of capacitance between an insulated wire and a ground caused by changes in the dielectric value of the surrounding material.

BACKGROUND OF THE INVENTION

The use of a capacitance probe to measure liquid levels has been disclosed in the prior art. For instance, in U.S. Pat. Nos. 3,958,159 and 3,864,974 (Rauchwerger), a capacitance probe including a tensioned insulated wire is used to measure changes in the liquid level of a container in cooperation with an electrical circuit using active elements. Another capacitance sensor using a tightly stretched insulated wire disposed inside of a closed container is described in U.S. Pat. No. 4,025,846 (Franz et al). Other examples of capacitance probes are described in U.S. Pat. No. 2,774,959 (Edelman et al) and U.S. Pat. No. 3,878,719 (Luttmann et al).

In addition, the circuit disclosed in the Rauchwerger patents referred to above, circuits which are used with a capacitance probe are disclosed in other patents. For instance, in U.S. Pat. No. 3,918,306 (Maltby), an impedance sensing network is used to measure transmission fluid level. A resistance-capacitance network is disclosed in U.S. Pat. No. 4,010,650 (Piatkowski, Jr.) for determining the liquid level in a reservoir. Another measuring apparatus which utilizes a capacitance transducer and associated circuit is disclosed in U.S. Pat. No. 4,086,528 (Walton).

SUMMARY OF THE INVENTION

In accordance with the present invention, a capacitance probe sensor device is provided for determining changes in capacitance of the device in an environment. The device includes a probe means having a poly(vinylidene fluoride) insulated wire and a metallic ground electrode spaced from the wire. The probe means senses the change in capacitance between the insulated wire and the ground electrode. An electrical signaling means, including an oscillator and a passive capacitance-resistance network, is electrically connected to the probe means to produce a linear output voltage proportional to the change in capacitance between the insulated wire and the ground electrode.

The provision of a poly(vinylidene fluoride) insulated wire as part of the probe means enables the probe to be used in a number of different applications. In one embodiment, the device is used to measure the level of water in a tank. One disadvantage of similar prior art capacitance probe devices wherein an insulated wire extends into the water over a long period of time is the deterioration of the insulation or polarization of the wire. This disadvantage of the prior art is overcome by the use of the insulated probe wire of the invention. Further, the insulation used also wraps tightly around the wire to prevent polarization. Other examples of applications of the present invention include the use thereof as a soil moisture meter, as a snow or water precipitation meter and to measure oil level, and as a flow rate meter and displacement measurement device.

The sensitivity of the passive capacitance-resistance network of the present invention can be easily changed so that a wide range of measurements can be effected. This allows the device to be used in the variety of different materials mentioned above. In addition, polarization of the probe is eliminated by dc decoupling of the probe.

Other features and advantages of the present invention will be set forth in or apparent from the detailed description of the preferred embodiments of the invention found hereinbelow.

DETAILED DESCRIPTION OF THE PREFERRED EMBODIMENTS

Figure 1:
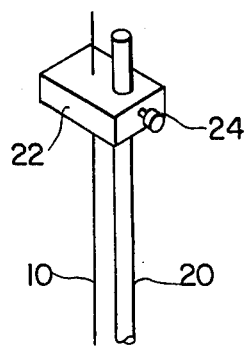
FIG. 1 is a perspective view of one embodiment of the capacitance probe of the present invention.

With reference now to the drawings in which like numerals represent like elements throughout the several views, a first embodiment of the present invention is in FIG. 1. The capacitance probe of this embodiment comprises a KYNAR insulated wire 10 which expands parallel to a metallic ground electrode 20 formed of a ¼" brass rod, and held taut between a brass peg and an adjustable wire holder 22 made of Lucite. Peg 21 is rigidly soldered in a hole 23 in ground electrode 20. Wire holder 22 is adjustably mounted on ground electrode 20 by means of a set screw 24. The capacitance between insulator wire 10 and ground electrode 20 varies with respect to the conductivity of the material between them. Thus, if the probe of this embodiment is partially immersed in a dielectric fluid such as a body of water, the capacitance between insulated wire 10 and ground electrode 20 varies with respect to the length of insulated wire 10 and ground electrode 20 which is submerged. By measuring the change in capacitance, the change of the level of the water can be determined and thus the probe acts as a water level sensing device.

Figure 2:
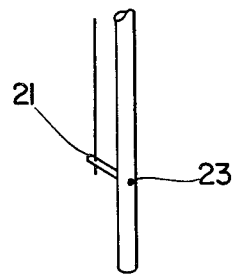
FIG. 2 is a cross-sectional view of the KYNAR insulated wire used in the capacitance probe of the present invention.

The KYNAR insulated wire 10 is depicted in FIG. 2. The insulated wire 10 comprises a metallic wire portion 11 which is completely surrounded by a tight fitting KYNAR insulating sleeve or coating 12. KYNAR is the trademark of the Pennsalt Co. for the generic material polyvinylidene fluoride or poly(vinylidene fluoride). The KYNAR insulation 12 acts to insulate wire portion 11 from whatever external material insulated wire 10 comes in contact with and KYNAR is chosen because of the stability thereof under water contact for long periods of time, i.e., KYNAR does not deteriorate under prolonged contact with water. In addition, KYNAR can be tightly wrapped around wire portion 11 to prevent polarization. It will be appreciated that a variety of different thicknesses can be used for wire portion 11 and KYNAR insulation 12 depending on the circumstances and taking into consideration the fact that capacitance will vary according to the diameter of wire portion 11 and the thickness of KYNAR insulation 12. A satisfactory insulated wire 10 is AWG 30 KYNAR wire which has a capacitance of one pico farad per mm of wire length.

Figure 3:
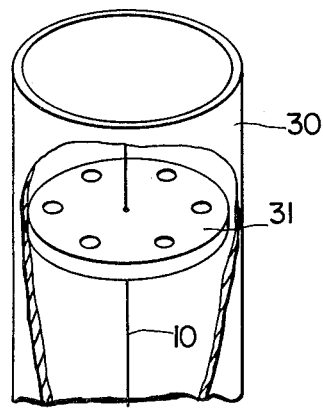
FIG. 3 is a partially cut-away perspective view of another embodiment of the present invention.

Another second embodiment of the present invention which is used as a fluid level measuring device, is depicted in FIG. 3. In this embodiment, insulated wire 10 is suspended inside of a ground electrode 30. Ground electrode 30 is made from a hollow metal tube which provides both a symmetrical grounding and shielding. A Lucite disc 31 is used for filtering action of high turbulent water flow and to space insulated wire 10 in the middle of ground electrode 30. A Lucite weight 32 attached to wire 10 also acts to space insulated wire 10 as well as to pull down on insulated wire 30 to hold it taut. A plurality of perforations 33 in both disc 31 and weight 32 provides filtering action and allows a fluid to pass therethrough.

Figure 4:
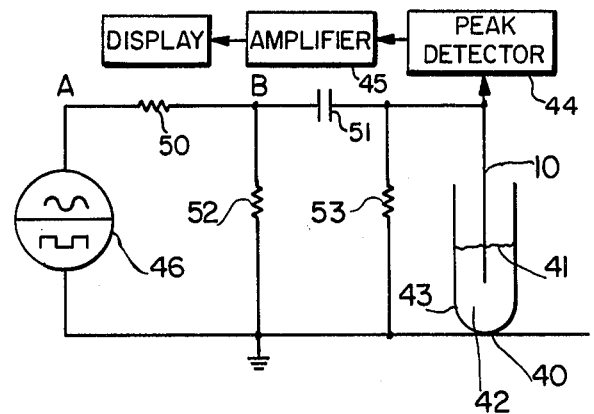
FIG. 4 is a schematic circuit diagram of the electrical signal processing network of the present invention.

Referring to FIG 4, a circuit diagram of an electrical signal processing network of the present invention is shown. The capacitance between insulated wire 10 and a ground electrode indicated at 40, referred to hereinafter as the probe capacitance, is used to determine the height 41 of water 42 in a container 43, the container 43 serving as the ground electrode in this embodiment. The circuit includes an oscillator 46 which is capable of generating an ac voltage or digital (pulsed) voltage waveform. The output of oscillator 46 is connected through a series resistor 50 and a series capacitor 51 to insulated wire 10, a first connection to ground being made from the junction between resistor 50 and capacitor 51 through a shunt resistor 52, a second connection to ground being made from the junction between capacitor 51 and insulated wire 10 through a shunt resistor 53. A peak detector connected to output terminal 44 rectifies the input signal from the circuit to provide a dc output corresponding to the peak of the input signal maximum amplitude. The output from the peak detector is then applied either to a differential amplifier 45, and to a visual display readout meter, or it may be outputted to a recorder (not shown) for display. The peak detector and amplifier can be like the same components described on pages 195 and 432, respectively, of the book on *Integrated Circuits Operational Amplifiers Cookbook*, by Walter G. Jung (1974) published by Howard W. Sams & Co., Inc. of Indianapolis, Ind.

In operation, the present invention, as shown in FIG. 4, functions in the following manner to measure the height of water in a container 43. First, the capacitance probe including insulated wire 10 is mounted in container 43 so that wire 10 will remain partially immersed over the range of water levels which are expected, and in this regard, the capacitance probe can be up to 10 m or more in length. The insulated wire 10 is connected to an output terminal 44 of the electrical network as shown in FIG. 4, and ground electrode 40 is connected to the electrical network as shown. As the height of water 42 varies inside of the container 43 which forms ground electrode 20, the resultant probe capacitance correspondingly changes. The change of capacitance is appreciable and readably measureable because the dielectric constant of water is 78.5 times that of air at 25° C.

The capacitance resistance network formed by capacitor 50, resistors 51, 52 and 53 functions to provide a linear output voltage in proportion to the change in probe capacitance, that is, the change in capacitance between insulated wire 10 and ground electrode 40. The linearity of output voltage signal is influenced by the wave shape of oscillator 46. It is noted that a square wave signal has a short linear range but good stability, while a sine wave signal has a greater linearity range but less stability, and thus either may be used depending on the circumstances. Resistors 50 and 52 serve a dual function: first, to provide proper signal reduction, and second, with capacitor 51 and the probe capacitance to assist in combination in producing a linear output. Resistor 52 also serves as part of the charge and discharge part of capacitor 51. Capacitor 51 serves to decouple the dc signal from the sensor wire 10, so as to prevent polarization of the probe capacitance. Resistor 53 also serves dual functions: first, to provide an ac path for capacitor 51 and the probe capacitance, and second, to assist in linearizing the output voltage of probe capacitance. Through experimentation, the following values have been found to provide a satisfactory operation of the electrical network shown in FIG. 4: 2.4 KHz for oscillator 46; 10 K ohms for resistor 50; 5 K ohms for resistors 52 and 53, and 0.01 uf for capacitor 51.

In operation, the signal from oscillator 46 is applied to the passive network composed of resistors 50, 52, and 53 and capacitor 51. The voltage appearing at point A is the oscillator voltage while the voltage at point B is proportional to the ratio of the values of resistors 50, 52, and 53, capacitor 51, and the probe capacitance. The output voltage at terminal 44 is thus proportional to the voltage at point B and the ratio of the values of capacitor 51, resistor 53, and the probe capacitance. As the probe capacitance changes, a signal phase shift is produced which changes the reflected load across the passive network of resistors 50, 52, and 53, and capacitor 51. The effect is a change of voltage at point B which tends to cancel output voltage at terminal 44 and assists in providing the desired linearity in the output voltage. It should be noted that the sensitivity of the circuit can be changed by changing the value of the four elements. The smaller the value of capacitor 51, the greater the sensitivity of the circuit.

Figure 5:
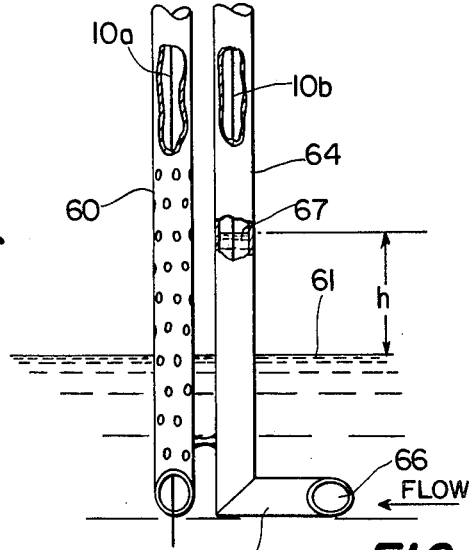
FIG. 5 is a perspective view of a rate of flow detector using the capacitance probe sensor of the present invention.

Another embodiment of the present invention is depicted in FIG. 5. In this embodiment, two separate capacitance probes are attached together and used to determine the rate of flow of a liquid. The first probe is formed from a perforated metal tube 60 in which a KYNAR wire 10a is mounted. This first probe acts to determine the level of the water 61. The second probe is formed from a metal tube 64 and has an elbow turn 65 with an open end 66 facing the flow of water. Inside of metal tube 64 is KYNAR wire 10b. The flow of water into open end 66 causes the level of the water 67 inside of metal tube 64 which is a distance h above the level of water 61. The distance h is a function of the rate of flow of the liquid, so that once the two water levels are determined by the first and second capacitance probes, respectively, the distance h, and hence the rate of flow, can also be calculated.

Figure 6:
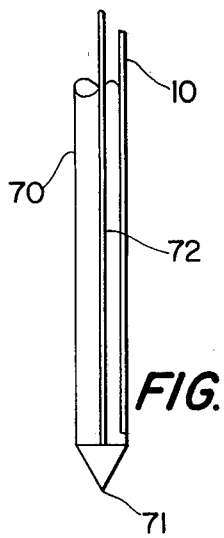
FIG. 6 is a perspective view of a moisture concentration measuring probe of the present invention for use in a solid material.

The present invention is also useable as a moisture content sensor in the form of an elongate capacitance probe 70 such as shown in FIG. 6. Capacitance probe 70 is made from an insulated material such as Lucite and has a tip 71 to facilitate placement of capacitance probe 70 in a solid material, such as soil. The KYNAR insulated wire 10, mounted flush with the surface of capacitance probe 70, runs along the length of capacitance probe 70. Running parallel to insulated wire 10 is a bare ground wire 72. Ground wire 72 is attached to the outer surface of capacitance probe 70 so that it is spaced from insulated wire 10. In operation, the capacitance between insulated wire 10 and ground wire 72 varies in accordance with the moisture content of the material surrounding capacitance probe 70. By measuring this variation in capacitance, the moisture content of the material (soil) is determined.

Figure 7:
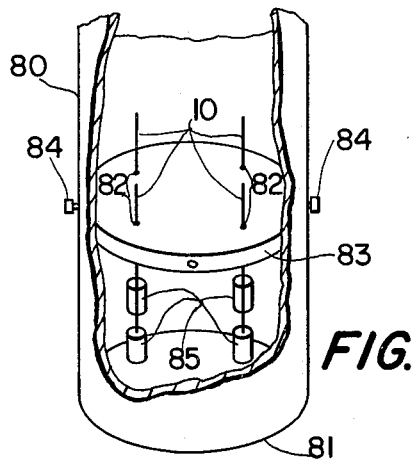
FIG. 7 is a partially cut-away perspective view of a displacement measuring device using capacitance probe sensors of the present invention.

The embodiment of the present invention depicted in FIG. 7 is used as a displacement sensor. Four KYNAR insulated wires 10 are suspended inside of a metal ground tube 80 with a sealed bottom 81. Insulated wires 10 are maintained spaced from each other as they pass through a set of guide holes 82 in a Lucite disc 83. Disc 83 is held in place inside of metal tube 80 by two set screws 84. Attached to the bottom end of each insulated wire 10 is a weight 85. In operation, as metal tube 80 is displaced from vertical, weights 85 cause the portions of insulated wires 10 below disc 85 to maintain their vertical orientation. Therefore, the capacitance between each insulated wire 10 and metal tube 80 changes. By monitoring the magnitude and direction of the changes in the capacitance of each insulated wire 10, the direction and amount of displacement of metal tube 80 can be determined.

Other alternative embodiments of the present invention should be apparent to those of ordinary skill in the art. For instance, the capacitance probe sensor device can be used in a barometer to determine the level of the fluid. The capacitance probe sensor device can also be used to monitor oil spills and to determine snow precipitation depth as well. Another application of this invention would be to determine perspiration rates. As a displacement sensor, the invention can be used to monitor water wave motions among other displacements which can be monitored.

Although the invention has been described in detail with respect to exemplary embodiments thereof, it will be understood by those of ordinary skill in the art that variations and modifications may be effected within the scope and spirit of the invention.

I claim:

1. Two capacitive probes used to determine the rate of flow of a liquid comprising:

a first capacitive probe having a metallic tube with perforations to permit the passage of a liquid therethrough and a wire electrode mounted in said tube to determine the vertical level of the liquid whose rate of flow is to be determined;

a second capacitive probe attached to said first probe, said second probe having a metallic liquid retaining tube with a bent section and an open end which faces the incoming flow of the liquid, said second probe also having a wire electrode, said second probe's metallic tube permitting the liquid to reach a height therein directly related to flow rate of the liquid being measured; and means for determining the difference in the vertical displacement of the liquids in said two probes by measuring the respective capacitance levels of the probes whereby the rate of flow of the liquid can be determined by ascertaining said difference.

2. The probes of claim 1 wherein each of the wire electrodes in the probes have an outer covering made of an insulating poly(vinylidene fluoride) material.

3. The probes of claim 2 wherein the bent section of the second probe is an elbow which terminates in said open liquid receiving end.

* * * * *